United States Patent [19]

Kimble

[11] Patent Number: 4,751,342
[45] Date of Patent: Jun. 14, 1988

[54] OXIDATIVE DEHYDROGENATION OF PARAFFINS

[75] Inventor: James B. Kimble, Bartlesville, Okla.

[73] Assignee: Phillips Petroleum Company, Bartlesville, Okla.

[21] Appl. No.: 99,888

[22] Filed: Sep. 22, 1987

[51] Int. Cl.$^4$ ............................................. C07C 5/18
[52] U.S. Cl. ..................................... 585/623; 585/658
[58] Field of Search ................................ 585/623, 658

[56] References Cited

U.S. PATENT DOCUMENTS

| | | | |
|---|---|---|---|
| 3,409,697 | 11/1968 | Callahan et al. | 260/680 |
| 3,789,017 | 1/1974 | Walker | 252/437 |
| 3,790,501 | 2/1974 | Walker | 252/437 |
| 3,852,369 | 12/1974 | Walker et al. | 260/680 E |
| 3,862,997 | 1/1975 | Walker | 585/623 |
| 4,044,066 | 8/1977 | Ripley | 260/680 E |
| 4,229,604 | 10/1980 | Timenov et al. | 585/445 |

*Primary Examiner*—Curtis R. Davis
*Attorney, Agent, or Firm*—K. K. Brandes

[57] ABSTRACT

In a process for dehydrogenating paraffins having from 2–12 carbon atoms per molecule (preferably propane and/or n-butane) to olefins, in the presence of free oxygen, steam and a catalyst comprising Ni, P, Sn, O and, optionally alkali metal, the improvement comprises having ammonia present at a $NH_3$:paraffin mole ratio of at least about 1:100.

15 Claims, No Drawings

OXIDATIVE DEHYDROGENATION OF PARAFFINS

BACKGROUND OF THE INVENTION

This invention relates to the oxidative dehydrogenation of paraffins in the presence of a catalyst comprising nickel, tin, phosphorus and oxygen.

The dehydrogenation of paraffins, in particular those having 2-12 carbon atoms per molecule, to mono- and diolefins in the presence of free oxygen, steam and a catalyst comprising nickel, tin, phosphorus, oxygen and, optionally, alkali metal is well known and has been described in U.S. Pat. Nos. 3,790,501 and 3,789,017. The present invention represents an improvement of these known oxidative dehydrogenation processes designed to minimize the formation of undesirable carbon oxides.

SUMMARY OF THE INVENTION

It is an object of this invention to catalytically dehydrogenate paraffins to olefins. It is another object of this invention to provide an improved oxidative dehydrogenation process employing a catalyst composition comprising nickel, tin, phosphorus and oxygen. Other objects and advantages will be apparent from the detailed description and the appended claims.

In accordance with this invention, a process for dehydrogenating paraffins comprises the step of substantially simultaneously (preferably simultaneously) contacting:
(A) a gaseous feed stream comprising at least one dehydrogenatable paraffin having from 2 to 12 (preferably 3-8) carbon atoms per molecule,
(B) a free oxygen containing gas;
(C) steam,
(D) an ammonia containing gas, and
(E) a catalyst composition comprising:
  (a) from about 20 to about 75 weight percent nickel,
  (b) from about 0.5 to about 10 weight percent phosphorus,
  (c) from about 1 to about 50 weight percent tin, and
  (d) oxygen combined with nickel, phosphorus and tin,
under such contacting conditions as to obtain a product stream comprising at least one olefin (i.e., monoolefin or diolefin or mixtures thereof preferably at least one monoolefin), having the same number of carbon atoms per molecule as said paraffin;
wherein the mole ratio of $NH_3$ to the dehydrogenatable feed paraffin is at least about 1:100.

In a preferred embodiment, the catalyst composition further comprises
(e) up to about 10 weight percent (i.e., 0 to about 10 weight-%) alkali metal (more preferably potassium), also being associated with catalyst component (d), i.e., oxygen.

DETAILED DESCRIPTION OF THE INVENTION

The catalyst composition used in the process of this invention can be prepared by any suitable means for combining catalyst components (a), (b), (c), (d) and, optionally, (e). Preferably, the catalyst composition used in the process of this invention is prepared by the method described in U.S. Pat. No. 3,790,501, herein incorporated as reference. Alternatively, yet less preferably, the catalyst composition can be prepared by the method described in U.S. Pat. No. 3,789,019, herein incorporated by reference. Any deviation in weight percentages of catalyst components (a), (b), (c), (d) and, optionally, (e) from those disclosed in the above-cited U.S. patents, if desired, can be accomplished by any one having ordinary skill in the art.

Preferred weight percentages of the various catalyst components are as follows; (a) about 25 to about 60, more preferably about 45 to about 57, weight-% Ni; (b) about 2 to about 8, more preferably 4 to about 6, weight-% P; (c) about 2 to about 40, more preferably about 5 to about 15, weight-% Sn; (e) about 0.1 to about 6; more preferably about 0.2 to about 2, weight-% alkali metal (most preferably K); and (d) as the balance.

Feed stream (A) can contain any suitable branched or unbranched dehydrogenatable paraffin (alkane) hydrocarbon having 2-12 carbon atoms per molecule. Non-limiting examples of said paraffins are listed in U.S. Pat. Nos. 3,789,017 and 3,790,501. One preferred paraffin is propane, which is at least partially dehydrogenated in the process of this invention to propylene. Another preferred paraffin is n-butane which is at least partially dehydrogenated in the process of this invention to butenes (butene-1 and/or butene-2), generally admixed with some butadiene. Feed Stream (A) can be a substantially pure stream of one vaporized paraffin or a vaporized mixture of two or more paraffins, optionally admixed with other gases, such as inert gases or olefins. It is within the scope of this invention, yet presently not preferred, to introduce a liquid paraffin stream into the contacting zone of the process of this invention, where it vaporizes before it contacts the other reagents and the catalyst composition.

The free oxygen containing gas (B) can be substantially pure oxygen gas; or it can be a mixture of $O_2$ with a substantially inert gas such as nitrogen (e.g., air). Stream (C) can be a stream of substantially pure steam, or it can be admixed with other gaseous substances, such as inert gases (e.g., nitrogen), or premixed with gas stream (B) and/or feed stream (A). The ammonia containing stream (D) can also be used in the process of this invention as a substantially pure gas stream of $NH_3$, or $NH_3$ can be admixed with an inert gas, or it can be premixed with feed stream (A) and/or a free oxygen containing gas and/or steam.

The preferred mole ratio of ammonia to feed paraffin is in the range of from about 1:20 to about 1:1, more preferably from about 1:10 to about 1:2, most preferably (in particular for n-butane) from about 1:10 to about 1:4. The preferred mole ratio of feed paraffin to free oxygen is in the range of from 1:10 to about 10:1, more preferably about 1:3 to about 2:1. The preferred mole ratio of feed paraffin to steam (vaporized water) is in the range of from about 1:50 to about 1:2, more preferably about 1:30 to about 1:5.

The dehydrogenatable paraffin feedstock is converted to olefins according to the processes of the present invention at temperatures in the range of from about 500° to about 1400° F., preferably from about 900° to about 1200° F., at any convenient pressure such as from about 5 to 250 psig, preferably about 7-20 psig. The feed rate the paraffin containing stream (A) will generally be in the range of from about 50 to about 5,000 GHSV (i.e., gas hourly space velocity, expressed as volume gaseous feed per volume catalyst per hour), preferably about 500-1500 GHSV. The fixed catalyst bed is the preferred mode of contact but other modes such as a fluidized bed can also be used. A continuous process is preferred.

The process is ordinarily carried out by forming a feed mixture, preferably a preheated mixture, of the dehydrogenatable feed (A), the oxygen containing gas, steam and ammonia, and passing this mixture over the catalyst at the desired temperature. The effluent from the reaction zone can be recovered, and subjected to any suitable separation means (such as fractional distillation, at atmospheric pressure or at elevated pressure) to isolate and recover the desired products (in particular monoolefins). Unconverted feed or partially converted materials can be recycled.

The catalyst used in the process of the present invention can be utilized for long periods of time without regeneration. However, when regeneration does become necessary, this can be simply accomplished by merely cutting off the flow of dehydrogenatable feedstock and ammonia and allowing the catalyst to be contacted with the oxygen and steam for a sufficient period of time at the above-cited reaction temperature to restore substantial activity to the catalyst.

An important objective of this invention is to reduce the amount of carbon oxides (CO and $CO_2$) formed in the process of this invention. One skilled in the art will generally optimize process conditions so as to maximize yields of desired olefins, and to minimize yields of undesirable by-products, in particular carbon oxides and cracked products (i.e., hydrocarbons having fewer carbon atoms per molecule than the feed paraffin).

The following examples are presented to further illustrate the invention without unduly limiting the scope of the invention, in particular to illustrate the effect of ammonia as co-feed on paraffin conversion and selectivity to desirable olefins and undesirable carbon oxides. Further optimization of process conditions of these examples is possible and is within the capability of any one having ordinary skill in the art.

EXAMPLE I

This example illustrates the dehydrogenation of a n-butane in the presence of free oxygen, steam, ammonia, (in invention runs) and a Ni/Sn/P/O/K catalyst composition.

The catalyst composition used was prepared substantially in accordance with the procedure of Example I of U.S. Pat. No. 3,790,501, with the exception that the weight percentages were varied. The catalyst employed in test runs of this example contained 53 weight-% Ni, 11.5 weight-% Sn, 5.3 weight-% P, about 1 weight-% K, and chemically bound oxygen as the balance.

4 grams of the catalyst were placed into a cylindrical quartz reactor having an inner diameter of about 0.3 inches and a height of about 6 inches.

A preheated gas stream of n-butane and a second preheated gas stream containing a mixture of oxygen, nitrogen, steam and, if desired, ammonia were continuously introduced at the top of the reactor. The flow rates of the individual feed gases were: 50 cc/minute n-butane, 50 cc/minute $O_2$, 120 cc/minute $N_2$ and 500 cc/minute steam. The flow rate of $NH_3$ was adjusted as as to provide the desired mole ratio of $NH_3$ to n-butane.

The quartz reactor was heated to the desired reaction temperature by means of an electric furnace, which surrounded the cylindrical quartz reactor. The product gas exited through a back pressure valve, which was set so as to provide a reaction pressure of about 3-4 psig. Generally the product gas was vented. A slip stream of the product gas was passed, at intervals of 20-40 minutes, through a gas chromatograph for analysis. Average test results are summarized in Table I.

TABLE I

|  | Run 1 (Control) | Run 2 (Invention) | Run 3 (Invention) | Run 4 (Invention) |
|---|---|---|---|---|
| Mole Ratio $NH_3:C_4H_{10}$ | 0:10 | 1:10 | 1:5 | 1:2.5 |
| Reaction Temp. (°C.) | 566 | 565 | 566 | 563 |
| % Conversion of n-Butane | 37 | 36.5 | 38 | 31 |
| % Yield of Butenes and Butadiene | 26.6 | 27.7 | 29.6 | 26.7 |
| % Selectivity[1] to: | | | | |
| Butenes and Butadiene | 72 | 76 | 78 | 86 |
| $CO_2$ and CO | 21 | 17 | 15 | 9 |
| Ethylene | 5 | 4 | 5 | 4 |

[1]Yield of Product ÷ Conversion × 100.

Test results in Table I show that the production of undesirable carbon oxides decreased with increasing $NH_3$:butane ratio, whereas the selectivity to butenes (butene-1, butene-2, isobutene, butadiene) increased with increasing $NH_3$:butane ratio. The highest yield of butenes and butadiene was attained at a $NH_3$:butane mole ratio of about 1:10 to about 1:5. Based on these test results, a $NH_3$:butane mole ratio of about 1:10 to about 1:4 is presently considered the preferred range.

EXAMPLE II

This example illustrates the use of propane as feed gas in the process of this invention. The experimental setup was essentally the same as described for Example I, with the exception that propane was used as feed hydrocarbon in lieu of n-butane. Test results are summarized in Table II.

TABLE II

|  | Run 5 (Control) | Run 6 (Invention) | Run 7 (Invention) | Run 8 (Invention) |
|---|---|---|---|---|
| Mole Ratio $NH_3:C_3H_8$ | 0:10 | 1:10 | 1:5 | 1:2.5 |
| Reaction Temp. (°C.) | 568 | 568 | 567 | 564 |
| % Conversion of Propane | 32 | 31 | 30 | 28 |
| % Yield of Propylene | 14.1 | 13.3 | 15.6 | 17.9 |
| % Selectivity to: | | | | |
| Propylene | 44 | 46 | 52 | 64 |
| CO + $CO_2$ | 39 | 36 | 30 | 21 |
| Ethylene | 13 | 13 | 13 | 11.5 |
| Methane | 4 | 3.5 | 3.5 | 3.5 |

The above test runs with propane as feed hydrocarbon were repeated with a flow rate of 30 cc/minute $O_2$ (in lieu of 50 cc/minute $O_2$ in Runs 5-8). Test results are summarized in Table III.

TABLE III

|  | Run 9 (Control) | Run 10 (Invention) | Run 11 (Invention) |
|---|---|---|---|
| Mole Ratio $NH_3:C_3H_8$ | 0:10 | 1:10 | 1:2.5 |
| Reaction Temp. (°C.) | 566 | 564 | 565 |
| % Conversion of Propane | 27 | 28 | 28 |
| % Yield of Propylene | 12.4 | 14.6 | 18.8 |
| % Selectivity to: | | | |
| Propylene | 46 | 52 | 67 |
| CO + $CO_2$ | 35 | 30 | 16 |
| Ethylene | 14.5 | 13.5 | 12 |
| Methane | 4.0 | 4.5 | 4.0 |

Test results in Tables II and III show that the presence of $NH_3$ had several beneficial effects: substantially enhanced propylene yield and selectivity, substantially reduced selectivity to carbon oxides, and a slight decrease in the selectivity to cracked products, in particular ethylene.

Reasonable variations, modifications and adaptations for various usages and conditions can be made within the scope of the disclosure and the appended claims, without departing from the scope of this invention.

That which is claimed is:

1. A process for dehydrogenating paraffins comprising the step of substantially simultaneously contacting
   (A) a gaseous feed stream comprising at least one dehydrogenatable paraffin having from 2 to 12 carbon atoms per molecule,
   (B) a free oxygen containing gas,
   (C) steam,
   (D) an ammonia containing gas, and
   (E) a catalyst composition comprising:
      (a) from about 20 to about 75 weight percent nickel,
      (b) from about 0.5 to about 10 weight percent phosphorus,
      (c) from about 1 to about 50 weight percent tin, and
      (d) oxygen combined with nickel, phosphorus and tin, under such contacting conditions as to obtain a product stream comprising at least one olefin having the same number of carbon atoms per molecule as said dehydrogenatable paraffin;
   wherein the mole ratio of ammonia to said dehydrogenatable paraffin is at least about 1:100.

2. A process in accordance with claim 1, wherein said catalyst composition additionally comprises up to about 10 weight-% alkali metal, also being associated with said oxygen.

3. A process in accordance with claim 1, wherein said catalyst composition comprises about 25-60 weight-% Ni, about 2-8 weight-% P, about 2-40 weight-% Sn, and about 0.1-6 weight-% K.

4. A process in accordance with claim 1, wherein said at least one dehydrogenatable paraffin has from 3 to 8 carbon atoms per molecule.

5. A process in accordance with claim 4, wherein said at least one dehydrogenatable paraffin is selected from the group consisting of propane and n-butane.

6. A process in accordance with claim 1, wherein said contacting conditions comprise a mole ratio of ammonia to said at least one dehydrogenatable paraffin is in the range of from about 1:20 to about 1:1.

7. A process in accordance with claim 6, wherein said dehydrogenatable paraffin is propane, and said mole ratio is in the range of from about 1:10 to about 1:2.

8. A process in accordance with claim 6, wherein said dehydrogenatable paraffin is n-butane, and said mole ratio is in the range of from about 1:10 to about 1:4.

9. A process in accordance with claim 1, wherein said contacting conditions comprise a reaction temperature in the range of from about 500° to about 1400° F., and a pressure in the range of from about 5 to about 250 psig.

10. A process in accordance with claim 9, wherein said contacting conditions comprise a gas hourly space velocity of said feed stream comprising at least one dehydrogenatable paraffin is in the range of from about 50 to about 5,000 volume feed/volume catalyst/hour.

11. A process in accordance with claim 1, wherein the mole ratio of said dehydrogenatable paraffin to free oxygen is in the range of from about 1:10 to about 10:1.

12. A process in accordance with claim 1, wherein the mole ratio of said dehydrogenatable paraffin to steam is in the range of from about 1:50 to about 1:2.

13. A process in accordance with claim 1, wherein said contacting conditions are such as to minimize the formation of carbon oxides.

14. A process in accordance with claim 1, wherein said contacting is carried out in a reactor containing a fixed bed of said catalyst composition.

15. A process in accordance with claim 1, wherein said product stream is subjected to separation means, and said at least one olefin is isolated and recovered.

* * * * *